United States Patent
Ciou et al.

(10) Patent No.: US 10,215,599 B2
(45) Date of Patent: Feb. 26, 2019

(54) FLUID SAMPLING SYSTEM AND FLUID SENSING DEVICE THEREOF

(71) Applicants: Acer Incorporated, New Taipei (TW); BENEPET CO., LTD, Taipei (TW)

(72) Inventors: Pu-De Ciou, New Taipei (TW); Shao-Chi Chuang, New Taipei (TW); Tsung-Hsun Wu, New Taipei (TW); Wei-Chen Lai, New Taipei (TW); Chun-Hung Wen, New Taipei (TW); Wen-Pin Chang, New Taipei (TW); Wen-Shu Lee, New Taipei (TW); Ta-Lun Tan, New Taipei (TW)

(73) Assignees: ACER INCORPORATED, New Taipei (TW); BENEPET CO., LTD, Taipei (TW)

( * ) Notice: Subject to any disclaimer, the term of this patent is extended or adjusted under 35 U.S.C. 154(b) by 0 days.

(21) Appl. No.: 15/955,957

(22) Filed: Apr. 18, 2018

(65) Prior Publication Data
US 2018/0306613 A1 Oct. 25, 2018

(30) Foreign Application Priority Data
Apr. 19, 2017 (TW) .............................. 106113057 A

(51) Int. Cl.
*G01F 1/06* (2006.01)
*G01F 1/28* (2006.01)
(Continued)

(52) U.S. Cl.
CPC .............. *G01F 1/065* (2013.01); *G01F 1/206* (2013.01); *G01F 1/28* (2013.01); *G01F 1/6965* (2013.01)

(58) Field of Classification Search
CPC . G01F 1/065; G01F 1/206; G01F 1/84; G01F 1/76
See application file for complete search history.

(56) References Cited

U.S. PATENT DOCUMENTS

| 4,801,897 A | * | 1/1989 | Flecken | G01F 1/8422 |
| | | | | 331/155 |
| 5,020,380 A | * | 6/1991 | Keita | G01F 1/8427 |
| | | | | 73/861.357 |

(Continued)

FOREIGN PATENT DOCUMENTS

| CN | 202693040 U | 1/2013 |
| JP | 2004-93544 A | 3/2004 |
| TW | M321522 | 11/2007 |

OTHER PUBLICATIONS

Chinese language office action dated Mar. 22, 2018, issued in application No. TW 106113057.

*Primary Examiner* — Jewel V Dowtin
(74) *Attorney, Agent, or Firm* — McClure, Qualey & Rodack, LLP

(57) ABSTRACT

A fluid sensing device is provided, including a main body and a light sensing unit. The main body includes a casing and a rotary member. A containing chamber is formed in the casing. The rotary member is rotatably disposed in the casing, and the rotary member has at least one transparent portion. A fluid flows into the containing chamber to drive the rotary member rotating around a central axis. The light sensing unit includes a first light transceiver module and a second light transceiver module disposed near the main body in an asymmetrical manner with respect to the central axis to transmit and receive the light passing through the translucent portion.

20 Claims, 8 Drawing Sheets

(51) Int. Cl.
*G01F 1/20* (2006.01)
*G01F 1/696* (2006.01)

(56) References Cited

U.S. PATENT DOCUMENTS 6,748,813 B1 * 6/2004 Barger ................. G01F 1/8409
  73/861.354
7,617,740 B2 * 11/2009 Zwikker ............... G01F 1/8413
  73/861.355

* cited by examiner

FLUID SAMPLING SYSTEM AND FLUID SENSING DEVICE THEREOF

CROSS REFERENCE TO RELATED APPLICATIONS

This application claims the benefit of Taiwan Patent Application No. 106113057, filed Apr. 19, 2017, the entirety of which is incorporated by reference herein.

BACKGROUND OF THE DISCLOSURE

Field of the Disclosure

The present disclosure relates to a fluid sampling system and a fluid sensing device thereof, and more particularly to a fluid sampling system and a fluid sensing device capable of sensing the flow direction of the fluid.

Description of the Related Art

There are a lot of experiments with fluids being conducted in labs today, such as mixing, dilution, or separation of blood and various bodily fluids, and so on. A proper instrument is needed to conduct those experiments in practice.

Please refer to FIG. 1, which is a diagram of a conventional fluid instrument 10. As an example, the fluid instrument 10 is a fluid sampling instrument or a fluid mixing instrument, which mainly includes a tank 20, a first tube 21, a second tube 22, a first fluid tank 41, a second fluid tank 42, a first valve 31 and a second valve 32. The first tube 21 is communicated to the first fluid tank 41 and the tank 20, and the second tube 22 is communicated to the second fluid tank 42 and the tank 20. The first valve 31 controls the flow of a fluid A between the first fluid tank 41 and the tank 20 through the first tube 21, and the second valve 32 controls the flow of a fluid B between the second fluid tank 42 and the tank 20 through the second tube 22.

During the procedure of the experiment, for example, when the tank 20 extracts fluid A from the first fluid tank 41, the first valve 31 is open and the second valve 32 is closed, so that fluid B cannot flow to the tank 20 through the second tube 22, and the tank 20 only extracts fluid A. However, the first valve 31 and the second valve 32 may not be able to close completely after being used repeatedly, resulting in unnecessary fluid leakage or reverse flow in the experiment. For example, when the tank 20 extracts fluid A from the first fluid tank 41, the second valve 32 may not be able to close completely so that some of fluid B also flows into the tank 20, resulting in experimental errors or inaccuracies.

Consequently, a sensing device capable of monitoring the unnecessary flow of a fluid and notifying the user is an important subject for further research and development.

BRIEF SUMMARY OF THE DISCLOSURE

Therefore, the present disclosure provides a fluid sensing device to solve the aforementioned problems.

According to some embodiments of the disclosure, the fluid sensing device includes a main body and a light sensing unit. The main body includes a hollow casing, a rotary member, a first tube and a second tube. A containing chamber is formed in the casing. The rotary member is rotatably disposed in the casing, and the rotary member has at least one transparent portion. The first tube and a second tube are communicated to the containing chamber. A fluid flows into the containing chamber through the first tube to drive the rotary member to rotate around a central axis, and then flows out of the containing chamber through the second tube. The light sensing unit includes a first transceiver module and a second light transceiver module disposed near the main body in an asymmetrical manner with respect to the central axis. The first light transceiver module includes a first light emitter and a first light receiver, the second light transceiver module includes a second light emitter and a second light receiver, and the first and second light receivers are configured to respectively receive a first light and a second light emitted from the first and second light emitters and passing through the transparent portion.

In some embodiments, the rotary member includes a plurality of protruding fan blades, wherein the angles formed between every two adjacent protruding fan blades are the same, and the rotary member is divided into a plurality of fan areas by the protruding fan blades.

In some embodiments, the rotary member includes two transparent portions, disposed on two adjacent fan-shaped areas.

In some embodiments, the rotary member comprises four or five protruding fan blades, the angles formed between every two adjacent protruding fan blades are the same, and the rotary member is divided into four or five fan-shaped areas by the protruding fan blades.

In some embodiments, each of the first tube and the second tube includes a converging structure, connected to the casing and communicated with the containing chamber.

In some embodiments, a fluid sampling system is provided and includes a valve, a base, an aforementioned fluid sensing device and a fluid driving unit. The fluid driving unit is disposed on the base for injecting the fluid into the containing chamber through the valve or discharging the fluid from the containing chamber through the valve.

In some embodiments, the fluid sampling system further includes a processing unit, configured to receive an electronic signal generated by the light sensing unit and to determine the rotating direction or the rotating speed of the rotary member according to the electronic signal.

In some embodiments, when the processing unit determines that the rotating direction of the rotary member is different from a preset rotating direction, the processing unit transmits a control signal to a display screen on the base, so that the display screen displays a warning message.

In some embodiments, when the processing unit determines that the rotating speed of the rotary member is different from a preset rotating speed, the processing unit transmits a control signal to a display screen on the base, so that the display screen displays a warning message.

In some embodiments, the fluid driving unit comprises a stepping motor.

The disclosure provides a fluid sensing device, connected between the tank and external containing tanks. When the fluid flows between the tank and external containing tanks, the rotating direction of the rotary member can be detected by the light sensing unit, and then the processing unit can determine whether the rotating direction is an unexpected rotation or is different from a preset rotating direction. When the rotating direction is the unexpected rotation or is different from the preset rotating direction, the processing unit controls the display screen to display a warning signal, so as to inform the user. Therefore, the present disclosure can solve the conventional problem of the driving motor of the experimental instrument not being able to correctly close the valve after being used for a long time, resulting in the unnecessary reverse flow of the fluid in the experiment.

Additional features and advantages of the disclosure will be set forth in the description which follows, and, in part, will be obvious from the description, or can be learned by practice of the principles disclosed herein. The features and advantages of the disclosure can be realized and obtained by means of the instruments and combinations particularly pointed out in the appended claims. These and other features of the disclosure will become more fully apparent from the following description and appended claims, or can be learned by the practice of the principles set forth herein.

DETAILED DESCRIPTION OF THE ILLUSTRATIVE EMBODIMENTS

Figure 1:
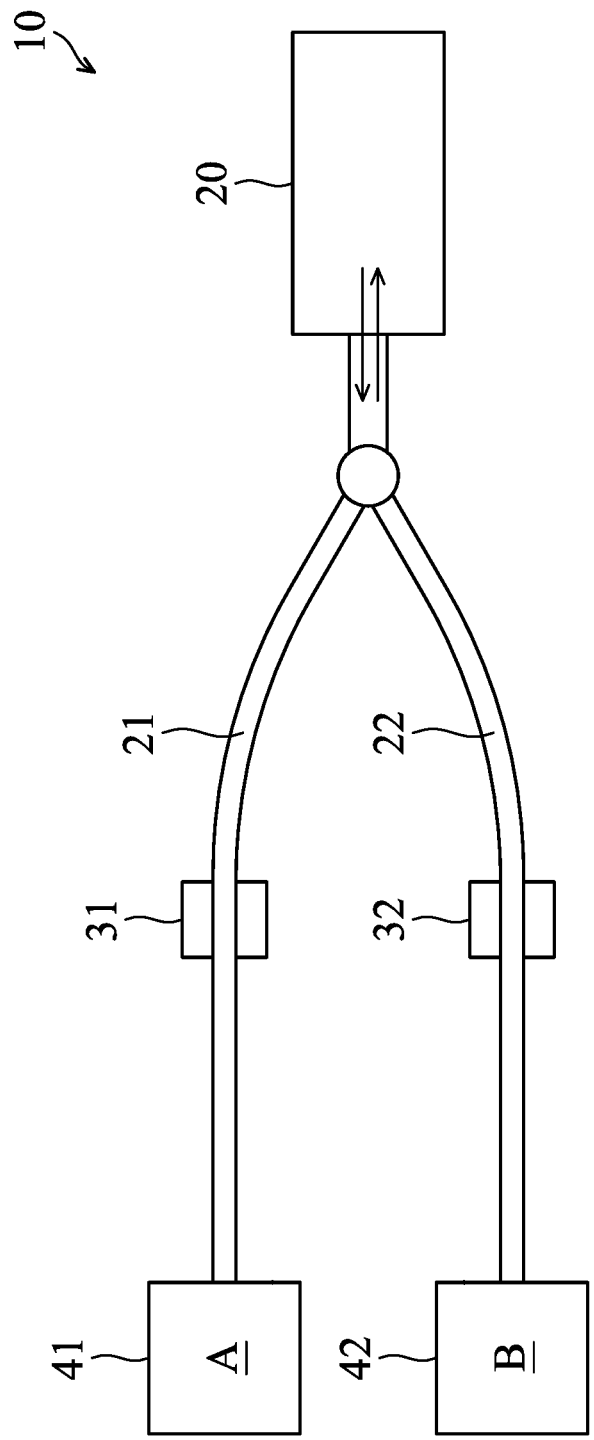
FIG. 1 is a diagram of a conventional fluid instrument.

In the following detailed description, for the purposes of explanation, numerous specific details and embodiments are set forth in order to provide a thorough understanding of the present disclosure. The specific elements and configurations described in the following detailed description are set forth in order to clearly describe the present disclosure. It will be apparent, however, that the exemplary embodiments set forth herein are used merely for the purpose of illustration, and the inventive concept may be embodied in various forms without being limited to those exemplary embodiments. In addition, the drawings of different embodiments may use like and/or corresponding numerals to denote like and/or corresponding elements in order to clearly describe the present disclosure. However, the use of like and/or corresponding numerals in the drawings of different embodiments does not suggest any correlation between different embodiments. The directional terms, such as "up", "down", "left", "right", "front" or "rear", are reference directions for accompanying drawings. Therefore, using the directional terms is for description instead of limiting the disclosure.

In this specification, relative expressions are used. For example, "lower", "bottom", "higher" or "top" are used to describe the position of one element relative to another. It should be appreciated that if a device is flipped upside down, an element at a "lower" side will become an element at a "higher" side.

The terms "about" and "substantially" typically mean +/−20% of the stated value, more typically +/−10% of the stated value and even more typically +/−5% of the stated value. The stated value of the present disclosure is an approximate value. When there is no specific description, the stated value includes the meaning of "about" or "substantially".

Figure 2:
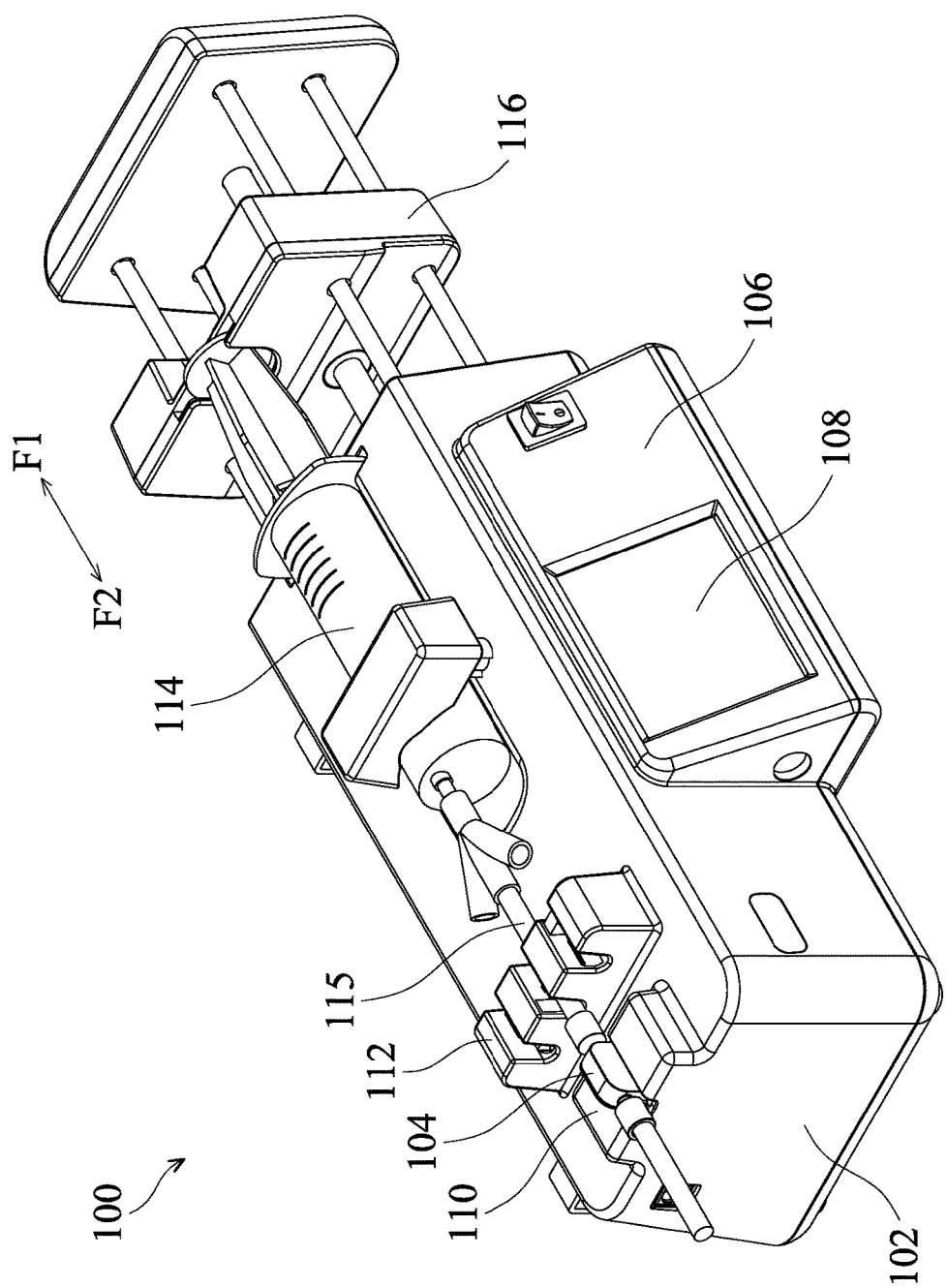
FIG. 2 is a diagram of a fluid sampling system according to an embodiment of the disclosure.

Please refer to FIG. 2, which is a diagram of a fluid sampling system 100 according to an embodiment of the disclosure. The fluid sampling system 100. The fluid sampling system 100 includes a base 102, a fluid sensing device 104, a processing unit 106 and a display screen 108. As shown in FIG. 2, an installation portion 110, a valve group 112 and a tank 114 are disposed on the base 102. The fluid sensing device 104 is disposed in the installation portion 110, and the fluid sensing device 104 is communicated to the tank 114 through a fluid tube 115. In this embodiment, the tank 114 can be a pump or a syringe with graduated marks, but it is not limited thereto.

In this embodiment, a driving motor is installed inside the base 102 (not shown in the figures) for driving a driving member 116 to move in a first direction F1 or a second direction F2 opposite to the first direction F1, so that the tank 114 can extract a fluid from an external container or discharge the fluid (the driving motor and the driving member 116 can constitute a fluid driving unit). The driving motor can be stepping motor, but it is not limited thereto. The processing unit 106 is electrically connected to the fluid sensing device 104, the driving motor and the display screen 108, and the processing unit 106 is configured to receive an electronic signal from the fluid sensing device 104 and can transmit a control signal to the driving motor or the display screen 108, so that the driving motor drives the driving member 116 to move, or the display screen 108 can display various information, such as the time at which the experiment is performed, the number of times which the experiment is performed, and so on. In addition, the processing unit 106 is also electrically connected to the valve group 112 and can transmit the control signal to the valve group 112, to open or close the valves of the valve group 112, so as to control the flow of the fluid between the fluid sensing device 104 and the tank 114.

Figure 3A:
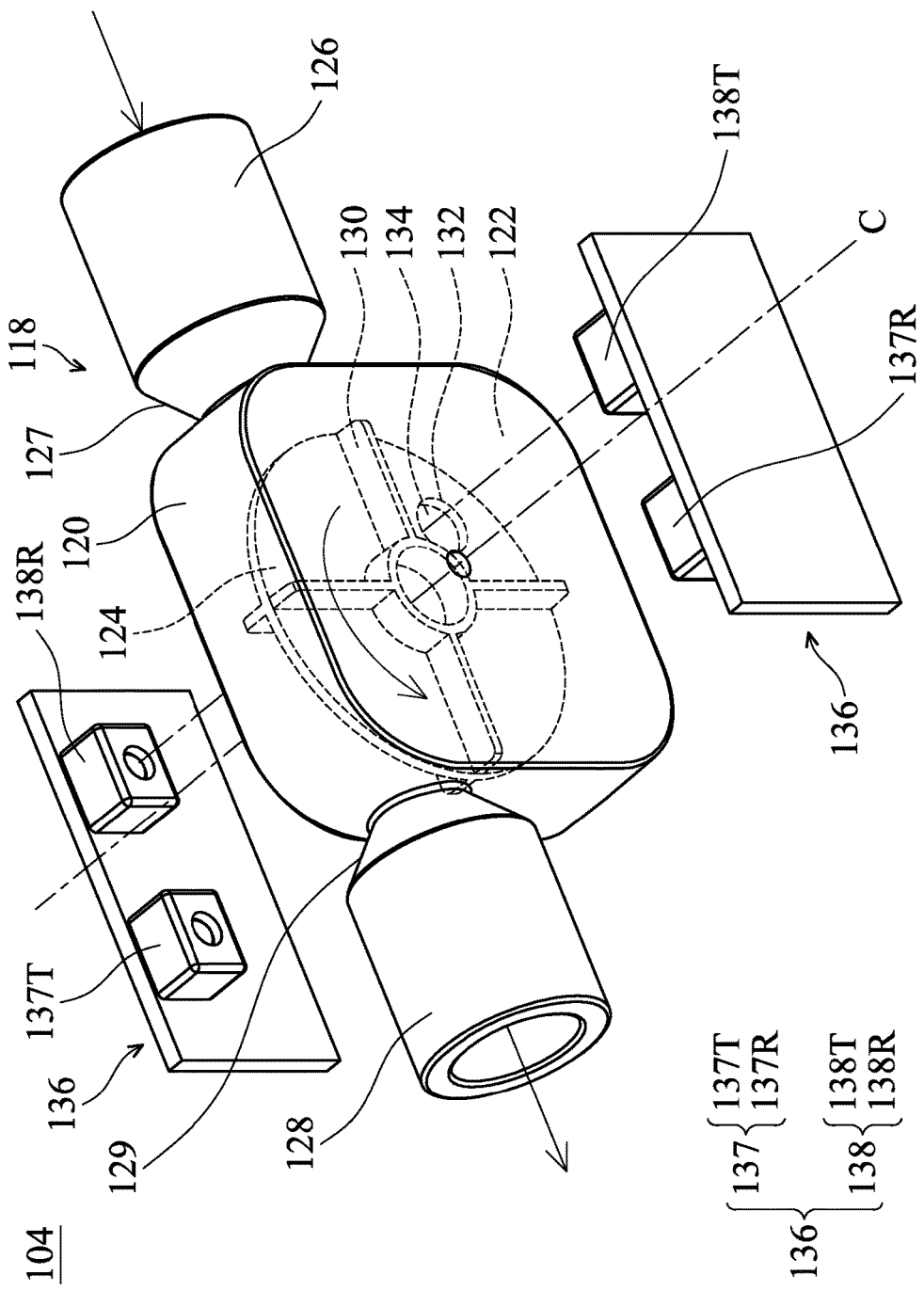
FIG. 3A is a diagram of the fluid sensing device according to an embodiment of the disclosure.
Figure 3B:
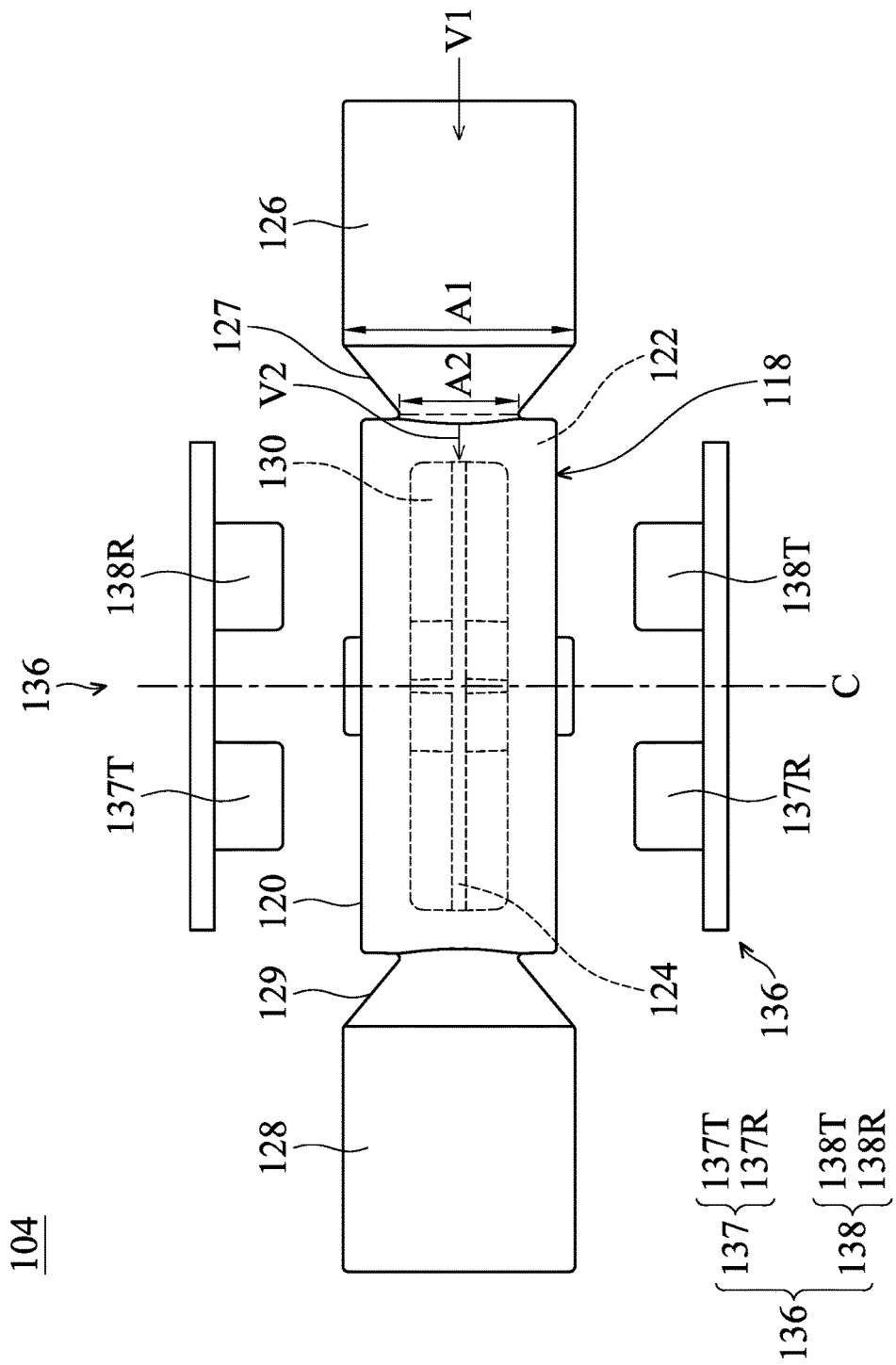
FIG. 3B is a top view of the fluid sensing device in FIG. 3A.
Figure 4B:
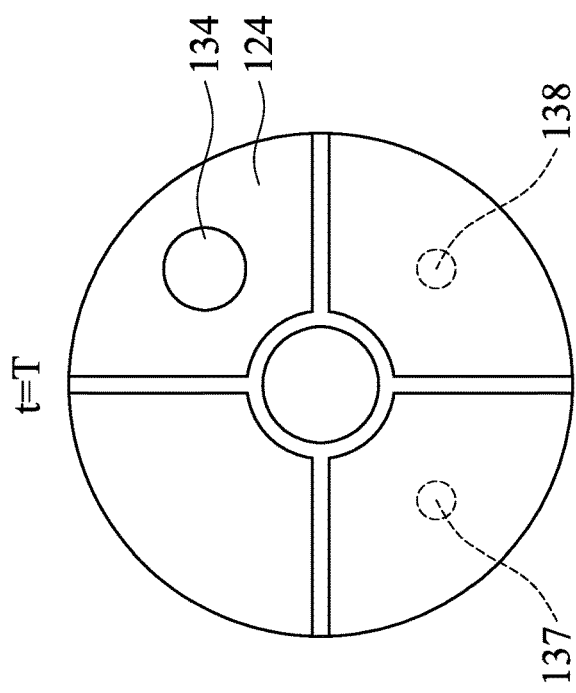
FIG. 4A to FIG. 4D are diagrams illustrating that the rotary member rotates to different positions according to an embodiment of the disclosure.
Figure 4A:
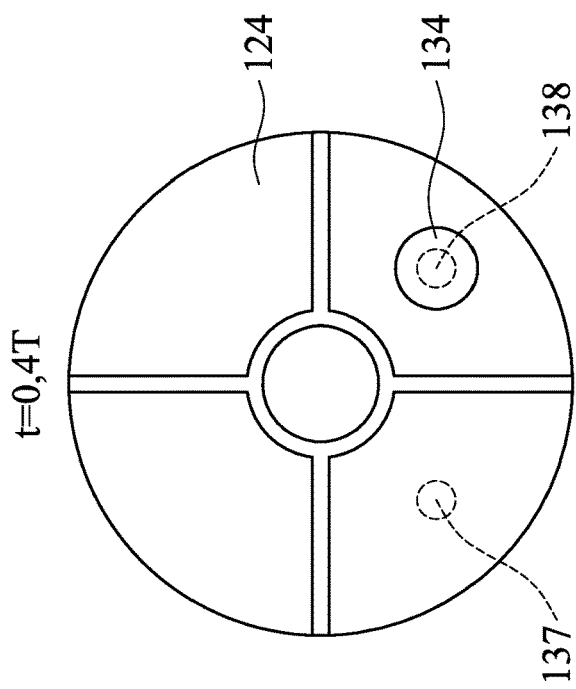
Figure 4D:
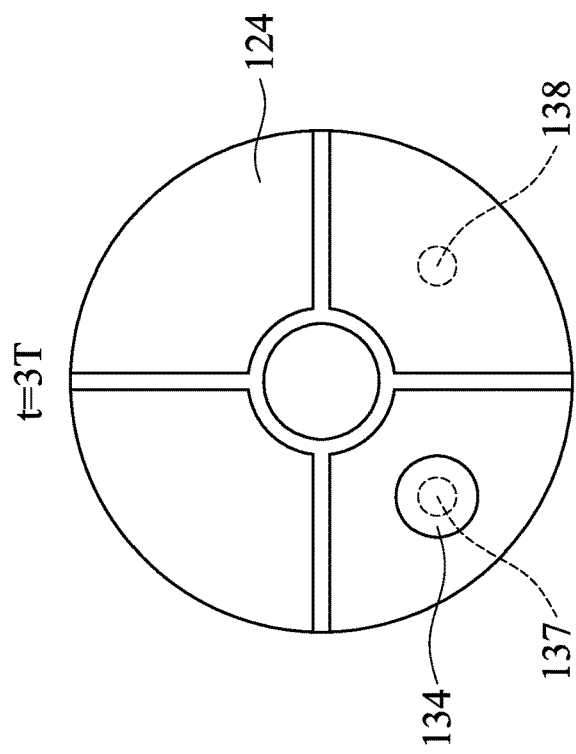
Figure 4C:
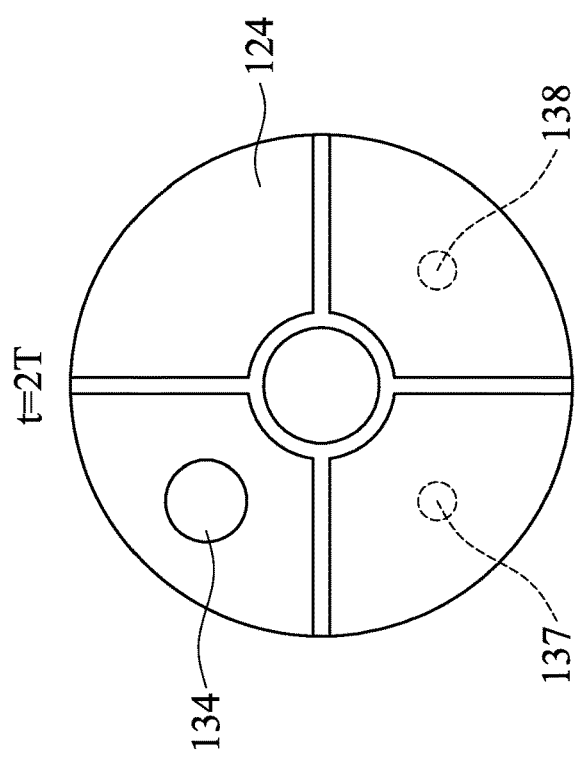

Please refer to FIG. 3A and FIG. 3B together. FIG. 3A is a diagram of the fluid sensing device 104 according to an embodiment of the disclosure, and FIG. 3B is a top view of the fluid sensing device 104 in FIG. 3A. As shown in the figures, the fluid sensing device 104 includes a main body 118 and a light sensing unit 136. The main body 118 includes a hollow casing 120, and a containing chamber 122 is formed in the casing 120. The casing 120 can be made of a translucent material, such as polyvinyl chloride (PVC), acrylonitrile-butadiene-styrene copolymer (ABS), polycarbonate (PC) or polypropylene (PP). In addition, the main body 118 further includes a rotary member 124, a first tube 126 and a second tube 128. The first tube 126 and the second tube 128 are disposed on two opposite sides of the casing 120 and are communicated to the containing chamber 122. The rotary member 124 is rotatably disposed in the casing 120. For example, a rotating shaft (not shown in the figures) is disposed in the casing 120 and is engaged with the rotary member 124, so that the rotary member 124 can rotate around a central axis C. The fluid can flow into containing chamber 122 through the first tube 126 so as to drive the rotary member 124 to rotate around the central axis C, and then the fluid flows out of the containing chamber 122 through the second tube 128 (the flow direction is indicated by the arrow in FIG. 3). It should be noted that, as shown in FIG. 3B, the first tube 126 includes a converging structure 127, and the second tube 128 includes a converging structure 129. The converging structure 127 and the converging structure 129 are connected to the casing 120 and are communicated to the containing chamber 122. The converging structure 127 has a maximum sectional area A1 and a minimum sectional area A2, and the minimum sectional area A2 is located on the position where the converging structure 127 is connected to the casing 120. When the fluid is incompressible and in a steady state, the product of a flow velocity V1 of the fluid passing by the maximum sectional area A1 which is multiplied by the maximum sectional area A1 is equal to the product of a flow velocity V2 of the fluid passing by the minimum sectional area A2 which is multiplied by the minimum sectional area A2 (that is, A1*V1=A2*V2). Because the maximum sectional area A1 is greater than the minimum sectional area A2, it can be known that the flow velocity V2 is greater than the flow velocity V1. When the flow velocity V1 of the fluid transported from the tank 114 to the first tube 126 is slow, the flow velocity of the fluid can be increased up to the flow velocity V2 due to the structural design of the converging structure 127 and the converging structure 129, so that the fluid can effectively drive the rotary member 124 to rotate.

The rotary member 124 can include four protruding fan blades 130, the angles formed between every two adjacent protruding fan blades 130 of the four protruding fan blades 130 are the same, and the rotary member is divided into four fan-shaped areas by the fan blades 130. The number of the fan blade 130 can also be two, three, or more than four. In addition, an opening 132 is formed in one of the four fan-shaped areas of the rotary member 124, so that light can travel through the opening 132 from one side to the other side of the rotary member 124. However, a transparent portion 134 with a transparent material can also be disposed inside the opening 132 of the rotary member 124, so that light can travel through the transparent portion 134.

The light sensing unit 136 is disposed near the main body 118 and includes a first light transceiver module 137 and a second light transceiver module 138. The first light transceiver module 137 and the second light transceiver module 138 are disposed on two sides of the main body 118 in an asymmetrical manner with respect to the central axis C. For example, in this embodiment, the first light transceiver module 137 is disposed on two opposite sides of the bottom left fan-shaped area of the rotary member 124 in FIG. 3A, and the second light transceiver module 138 is disposed on two opposite sides of the bottom right fan-shaped area of the rotary member 124. The first light transceiver module 137 includes a first light emitter 137T and a first light receiver 137R, and the second light transceiver module 138 includes a second light emitter 138T and a second light receiver 138R. The first light receiver 137R and the second light receiver 138R are configured to respectively receive a first light and a second light generated by the first light emitter 137T and the second light emitter 138T, and the first light and the second light travel through the transparent portion 134 in the opening 132.

Please refer to FIG. 4A to FIG. 4D, which are diagrams illustrating that the rotary member 124 rotates to different positions according to an embodiment of the disclosure. First, the rotating speed of the rotary member 124 is assumed to be a constant and the rotary member 124 is located on the position in FIG. 4A at time t=0. That is, the transparent portion 134 corresponds to the bottom right fan-shaped area. At this time, the second light receiver 138R of the second light transceiver module 138 can receive the second light traveling through the transparent portion 134 and generated by the second light emitter 138T. Next, the rotary member 124 rotates counterclockwise to the position illustrated in FIG. 4B at time t=T, so that the transparent portion 134 is located on the top right fan-shaped area. At this time, the first light receiver 137R and the second light receiver 138R cannot receive the first light and the second light from the first light emitter 137T and the second light emitter 138T. After that, the rotary member 124 continues to rotate to the position illustrated in FIG. 4C at time t=2T, and to the position illustrated in FIG. 4D at time t=3T. When time t=3T, the transparent portion 134 corresponds to the bottom left fan-shaped area, and the first light receiver 137R of the first light transceiver module 137 can receive the first light traveling through the transparent portion 134 and generated by the first light emitter 137T. Finally, the rotary member 124 rotates back to the position illustrated in FIG. 4A at time t=4T, so as to complete a cycle. That is, the transparent portion 134 moves back to the bottom right fan-shaped area.

During the procedure of rotation of the rotary member 124, the first light transceiver module 137 and the second light transceiver module 138 transmit electronic signals to the processing unit 106 when receiving the first light and the second light, and the processing unit 106 determines the rotating direction of the rotary member 124 according to the time point of receiving the electronic signals. For example, when the rotary member 124 rotates from the position in FIG. 4D to the position in FIG. 4A, the processing unit 106 can know that after a period of time T subsequent to the time point at which the first light transceiver module 137 receives the first light, the second light transceiver module 138 can receive the second light. Next, when the rotary member 124 continues to rotate from the position in FIG. 4A to the position in FIG. 4D, the processing unit 106 can know that after a period of time 3T subsequent to the time point at which the second light transceiver module 138 receives the second light, the first light transceiver module 137 can receive the first light. Therefore, the processing unit 106 can determine that the rotary member 124 rotates counterclockwise according to the electronic signals and the time points thereof. Conversely, after a period of time 3T subsequent to the time point at which the first light transceiver module 137 receives the first light, the second light transceiver module 138 receives the second light, or after a period of time T subsequent to the time point at which the second light transceiver module 138 receives the second light, the first light transceiver module 137 receives the first light, and then the processing unit 106 can determine that the rotary member 124 rotates clockwise.

Figure 5:
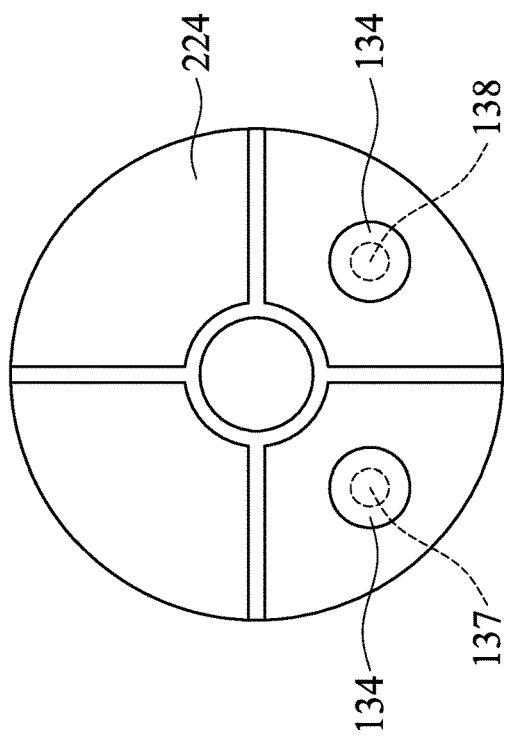
FIG. 5 is a diagram of a rotary member according to another embodiment of the disclosure.

Please refer to FIG. 5, which is a diagram of a rotary member 224 according to another embodiment of the disclosure. In this embodiment, the rotary member 224 can include two transparent portions 134 respectively disposed on two adjacent fan-shaped areas, and the first light transceiver module 137 and the second light transceiver module 138 are disposed on the positions corresponding to the two transparent portions 134. Similar to the previous embodiment, during the rotation procedure of the rotary member 224, the processing unit 106 can determine the rotating direction of the rotary member 224 according to the electronic signals generated by the first light transceiver module 137 and the second light transceiver module 138 and the time points thereof. The method of determining the rotating direction of the rotary member 224 is the same as that in the previous embodiment.

Figure 6:
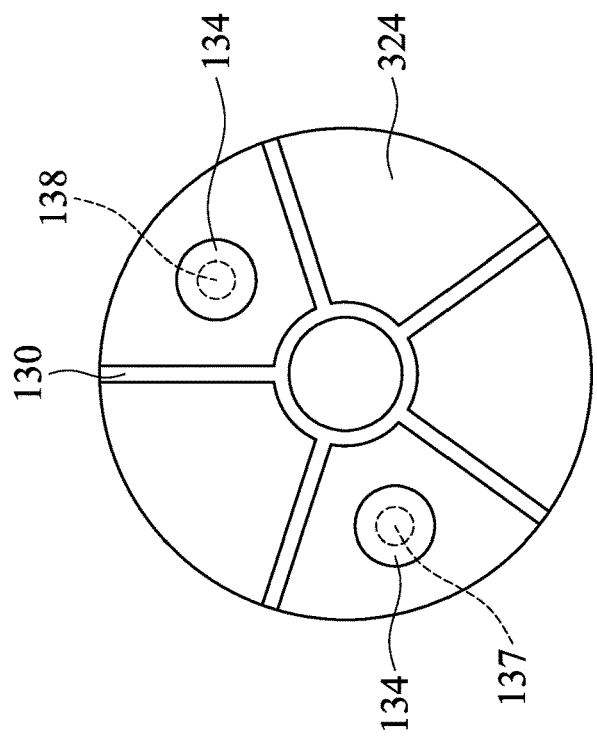
FIG. 6 is a rotary member according to another embodiment of the disclosure.

Please refer to FIG. 6, which is a rotary member 324 according to another embodiment of the disclosure. In this embodiment, the rotary member 324 includes five protruding fan blades 130. The angles formed between every two adjacent protruding fan blades 130 are the same, and the rotary member 324 is divided into five fan-shaped areas by the protruding fan blades 130. The rotary member 324 can include two transparent portions 134, the two transparent portions 134 are respectively disposed on the first fan-shaped area and the third fan-shaped area in this embodiment, and the first light transceiver module 137 and the second light transceiver module 138 are disposed on the positions corresponding to the two transparent portions 134. Similar to the previous embodiment, during the rotation procedure of the rotary member 324, the processing unit 106 can determine the rotating direction of the rotary member 324 according to the electronic signals generated by the first light transceiver module 137 and the second light transceiver module 138 and the time points thereof. The method of determining the rotating direction of the rotary member 224 is the same as that in the previous embodiment.

Figure 7:
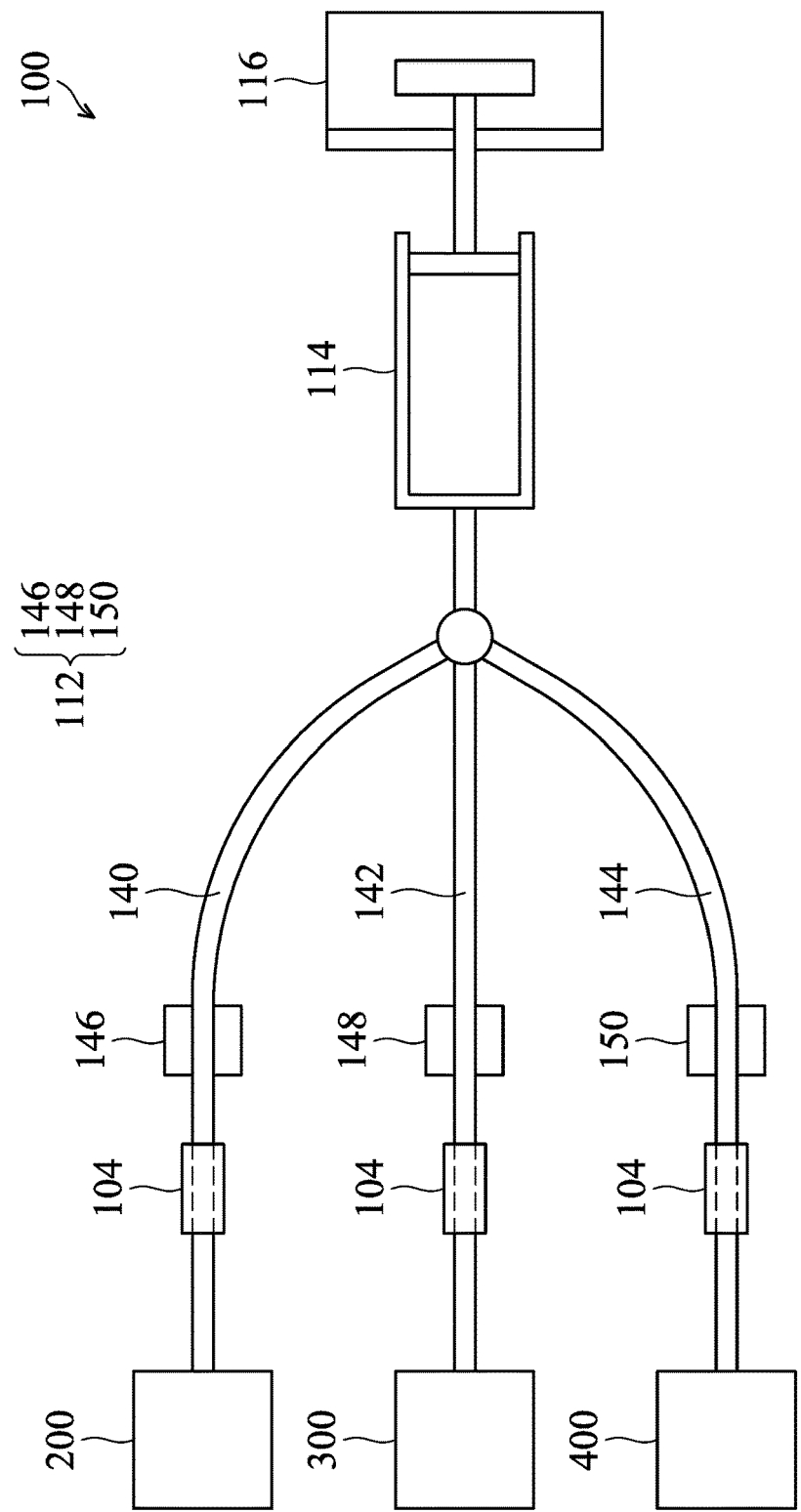
FIG. 7 is a diagram of a fluid sampling system which is connected to three external containing tanks according to an embodiment of the disclosure.

Please refer to FIG. 7, which is a diagram of a fluid sampling system 100 which is connected to three external containing tanks according to an embodiment of the disclosure. Some members are omitted herein for simplicity. In this embodiment, the tank 114 is respectively communicated to an external first containing tank 200, a second containing tank 300 and a third containing tank 400 through a first hose 140, a second hose 142 and a third hose 144. The valve group 112 includes a first valve 146, a second valve 148 and a third valve 150, which are configured to respectively control the flows in the first hose 140, the second hose 142 and the third hose 144. The fluid sampling system 100 can be a hemodialysis system for animals. The first containing tank 200 represents a bottle with the dialysate, the second containing tank 300 represents a body cavity of the animal, and the third containing tank 400 represents a waste liquid bottle. When the fluid sampling system 100 is utilized to perform the hemodialysis treatment, the processing unit 106 can control the first valve 146 to open, the second valve 148 and the third valve 150 to be closed, and controls the driving motor to drive the driving member 116 to move rightward, so that the dialysate in the first containing tank 200 is drawn to the tank 114. Then, the second valve 148 is open, the first valve 146 and the third valve 150 are closed, and the dialysate is injected from the tank 114 into the second containing tank 300 (the body cavity of the animal) by the driving member 116. When the dialysate is injected into the body cavity of the animal and mixed with the bodily fluid, the metabolic waste can be cleared because of the semipermeable property of the peritoneum. After that, the third valve 150 is open, and the first valve 146 and the second valve 148 are closed, so that the mixed waste bodily fluid can be discharged to the third containing tank 400, so as to complete one cycle of the hemodialysis treatment. It should be noted that the first hose 140, the second hose 142 and the third hose 144 are tightly connected to the corresponding fluid sensing devices 104, so as to ensure that the fluid therein does not contact the outside environment and is not contaminated. In addition, the first hose 140, the second hose 142 and the third hose 144 are disposable. For example, they are discarded after being used for 24-48 hours, and new tubes are replaced to prevent the same tube from being used for different animals, so as to ensure the safety of each hemodialysis treatment.

If the third valve 150 is not closed completely during the process of drawing the dialysate, the waste bodily fluid of the animal may also be drawn from the third containing tank 400 into the tank 114. At this time, the fluid sensing device 104 connected to the third hose 144 can detect the abnormal flow of the waste bodily fluid of the animal and generates the electronic signal to inform the processing unit 106. The processing unit 106 can determine that the rotation driven by the waste bodily fluid of the animal is an unexpected rotation according to the electronic signal. For example, the rotating speed of the rotary member 124 of the fluid sensing device 104 connected to the third hose 144 is different from a preset rotating speed. Then, the processing unit 106 transmits a control signal to the display screen 108, so that the display screen 108 displays a warning screen to inform the user that the third valve 150 malfunctions. In another embodiment, when the processing unit 106 determines that the rotating direction generated by the flow of the fluid is different from a preset rotating direction, the processing unit 106 also transmits the control signal to the display screen 108, so that the display screen 108 displays the warning screen.

In contrast to the prior art, the disclosure provides a fluid sensing device connected between the tank and external containing tanks. When the fluid flows between the tank and external containing tanks, the rotating direction of the rotary member can be detected by the light sensing unit, and then the processing unit can determine whether the rotating direction is an unexpected rotation or is different from a preset rotating direction. When the rotating direction is the unexpected rotation or is different from the preset rotating direction, the processing unit controls the display screen to display a warning signal, so as to inform the user. Therefore, the present disclosure can solve the conventional problem of the driving motor of the experimental instrument not being able to correctly close the valve after being used for a long time, resulting in the unnecessary reverse flow of the fluid in the experiment.

Although the embodiments and their advantages have been described in detail, it should be understood that various changes, substitutions, and alterations can be made herein without departing from the spirit and scope of the embodiments as defined by the appended claims. Moreover, the scope of the present application is not intended to be limited to the particular embodiments of the process, machine, manufacture, composition of matter, means, methods, and steps described in the specification. As one of ordinary skill in the art will readily appreciate from the disclosure, processes, machines, manufacture, compositions of matter, means, methods, or steps, presently existing or later to be developed, that perform substantially the same function or achieve substantially the same result as the corresponding embodiments described herein may be utilized according to the disclosure. Accordingly, the appended claims are intended to include within their scope such processes, machines, manufacture, compositions of matter, means, methods, or steps. In addition, each claim constitutes a separate embodiment, and the combination of various claims and embodiments are within the scope of the disclosure.

What is claimed is:
1. A fluid sensing device, comprising:
   a main body, comprising:
      a casing, wherein a containing chamber is formed in the casing; and
      a rotary member, rotatably disposed in the containing chamber, wherein the rotary member has at least one transparent portion;
   a first tube; and
   a second tube, wherein the first tube and the second tube are communicated with the containing chamber, wherein a fluid flows into the containing chamber through the first tube to drive the rotary member to rotate around a central axis, and then flows out of the containing chamber through the second tube; and
   a light sensing unit, comprising a first transceiver module and a second light transceiver module, disposed near the main body in an asymmetrical manner with respect to the central axis, wherein the first light transceiver module comprises a first light emitter and a first light receiver, the second light transceiver module comprises a second light emitter and a second light receiver, and the first and second light receivers are configured to respectively receive a first light and a second light emitted from the first and second light emitters and passing through the transparent portion.

2. The fluid sensing device as claimed in claim 1, wherein the rotary member comprises a plurality of protruding fan blades, wherein the angles formed between every two adjacent protruding fan blades are the same, and the rotary member is divided into a plurality of fan areas by the protruding fan blades.

3. The fluid sensing device as claimed in claim 2, wherein the rotary member comprises two transparent portions, disposed on two adjacent fan-shaped areas.

4. The fluid sensing device as claimed in claim 1, wherein the rotary member comprises four or five protruding fan blades, the angles formed between every two adjacent protruding fan blades are the same, and the rotary member is divided into four or five fan-shaped areas by the protruding fan blades.

5. The fluid sensing device as claimed in claim 1, wherein each of the first tube and the second tube comprises a converging structure, connected to the casing and communicated with the containing chamber.

6. The fluid sensing device as claimed in claim 1, wherein the casing is made of a translucent material.

7. The fluid sensing device as claimed in claim 6, wherein the casing is made of polyvinyl chloride (PVC), acrylonitrile-butadiene-styrene copolymer (ABS), polycarbonate (PC) or polypropylene (PP).

8. A fluid sampling system, comprising:
a base, comprising a valve;
a fluid sensing device as claimed in claim 1, disposed on the base; and
a fluid driving unit, disposed on the base, for injecting the fluid into the containing chamber through the valve or discharging the fluid from the containing chamber through the valve.

9. The fluid sampling system as claimed in claim 8, wherein the fluid sampling system further comprises a processing unit, configured to receive an electronic signal generated by the light sensing unit and to determine the rotating direction or the rotating speed of the rotary member according to the electronic signal.

10. The fluid sampling system as claimed in claim 9, wherein when the processing unit determines that the rotating direction of the rotary member is different from a preset rotating direction, the processing unit transmits a control signal to a display screen on the base, so that the display screen displays a warning message.

11. The fluid sampling system as claimed in claim 9, wherein when the processing unit determines that the rotating speed of the rotary member is different from a preset rotating speed, the processing unit transmits a control signal to a display screen on the base, so that the display screen displays a warning message.

12. The fluid sampling system as claimed in claim 8, wherein the fluid driving unit comprises a stepping motor.

13. The fluid sampling system as claimed in claim 8, wherein the casing is made of polyvinyl chloride (PVC), acrylonitrile-butadiene-styrene copolymer (ABS), polycarbonate (PC) or polypropylene (PP).

14. The fluid sampling system as claimed in claim 8, wherein the rotary member comprises a plurality of protruding fan blades, wherein the angles formed between every two adjacent protruding fan blades are the same, and the rotary member is divided into a plurality of fan areas by the protruding fan blades.

15. The fluid sampling system as claimed in claim 14, wherein the rotary member comprises two transparent portions, disposed on two adjacent fan-shaped areas.

16. The fluid sampling system as claimed in claim 8, wherein the rotary member comprises four or five protruding fan blades, the angles formed between every two adjacent protruding fan blades are the same, and the rotary member is divided into four or five fan-shaped areas by the protruding fan blades.

17. The fluid sampling system as claimed in claim 8, wherein each of the first tube and the second tube comprises a converging structure, connected to the casing and communicated with the containing chamber.

18. The fluid sampling system as claimed in claim 8, wherein the fluid sampling system further comprises a tank, communicated to the fluid sensing device, and the fluid is contained in the tank.

19. The fluid sampling system as claimed in claim 18, wherein the fluid sampling system comprises three fluid sensing devices, communicated to the tanks.

20. The fluid sampling system as claimed in claim 19, wherein the fluid sampling system further comprises three containing tanks, respectively connected to the fluid sensing devices.

* * * * *